United States Patent [19]
Winkler et al.

[11] Patent Number: 5,279,553
[45] Date of Patent: Jan. 18, 1994

[54] TRANSPYLORIC JEJUNOSTOMY CANNULATING SYSTEM

[75] Inventors: Martin J. Winkler, 6116 Chicago St., Omaha, Nebr. 68132; Christine Decaria, Los Altos, Calif.

[73] Assignee: Martin J. Winkler, Omaha, Nebr.

[21] Appl. No.: 862,430

[22] Filed: Apr. 2, 1992

[51] Int. Cl.$^5$ .................. A61M 31/00; A61M 5/178
[52] U.S. Cl. ........................ 604/53; 604/160; 604/164
[58] Field of Search ............ 604/158-170, 175, 178, 43, 45, 264, 280, 268, 185, 49, 51-53; 606/185

[56] References Cited

U.S. PATENT DOCUMENTS

| | | | |
|---|---|---|---|
| 3,459,189 | 8/1969 | Alley et al. | 604/166 |
| 3,653,388 | 4/1972 | Tenckhoff | 604/161 X |
| 3,742,958 | 7/1973 | Rundles | 604/160 X |
| 4,354,491 | 10/1982 | Marbry | 604/160 |
| 4,543,089 | 9/1985 | Moss | 604/93 |
| 4,581,025 | 4/1986 | Timmermans | 604/264 |
| 4,642,092 | 2/1987 | Moss | 604/43 |
| 4,685,901 | 8/1987 | Parks | 604/96 |
| 4,701,163 | 10/1987 | Parks | 604/178 |
| 4,810,244 | 3/1989 | Allen | 604/44 |
| 4,846,791 | 7/1989 | Hattler et al. | 604/43 |
| 4,867,745 | 9/1989 | Patel | 604/158 |
| 5,071,405 | 12/1991 | Piontek et al. | 604/96 |

FOREIGN PATENT DOCUMENTS

| | | | |
|---|---|---|---|
| 628292 | 10/1961 | Canada | 604/160 |
| 791563 | 6/1958 | France | 604/160 |

OTHER PUBLICATIONS

"The Moss G-Tube Peg Kit Has it all" advertisement referring to U.S. Pat. Nos. 4,543,089 and 4,642,092. (Four sheets describing Carey-Alzate-Coons Devil Lumen Gastrojejunostomy set, referring to Re. 131,855 and U.S. Pat. No. 4,581,025.), undated.

Primary Examiner—John D. Yasko
Assistant Examiner—Adam J. Cermak
Attorney, Agent, or Firm—John A. Beehner

[57] ABSTRACT

A transpyloric jejunostomy cannulating apparatus includes an abdominal wall trocar having an elongated shaft and a sharpened tapered end for passage through a patient's abdominal wall. A tubular sheath is telescopically slidable onto the trocar for passage through the abdominal wall with it. An elongated generally tubular gastrostomy introducer has one end adapted for connection to a suction source and a free end portion tapering toward a free end of reduced width for insertion through the gastric wall into the lumen of a stomach. The introducer has an inlet opening adjacent the free end for aspirating the stomach. An elongated slotted cannulator, generally c-shaped in cross section, has an external width for passage through the sheath and an internal width to accommodate passage of the introducer therethrough. The cannulator may be manipulated through the pylorus for directing an elongated flexible feed tube previously inserted through the sheath in the abdominal wall, through the gastric wall, pylorus and duodenum into the jejunum beyond the ligament of Treitz.

31 Claims, 10 Drawing Sheets

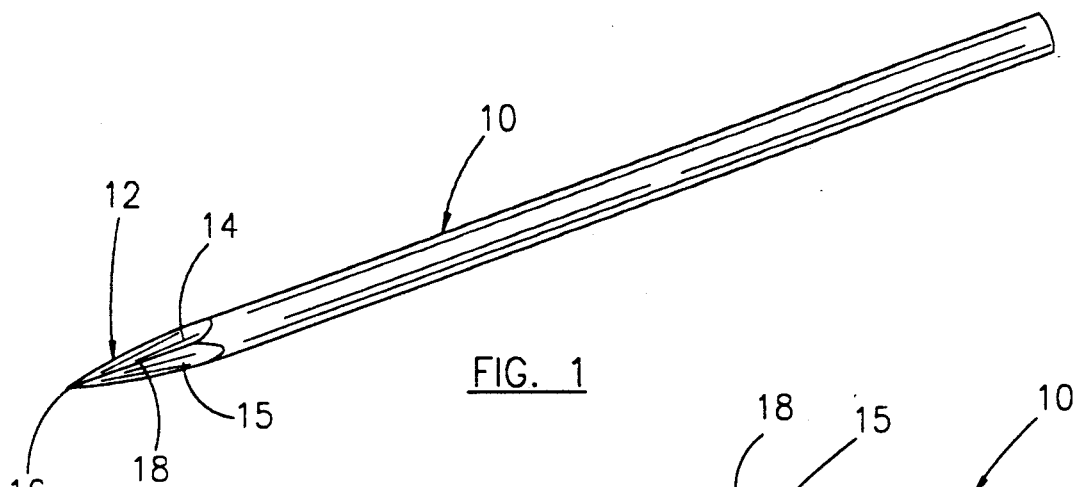
FIG. 1
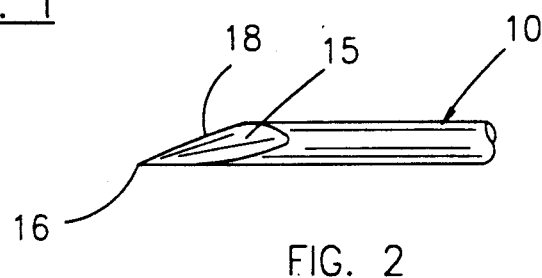
FIG. 2
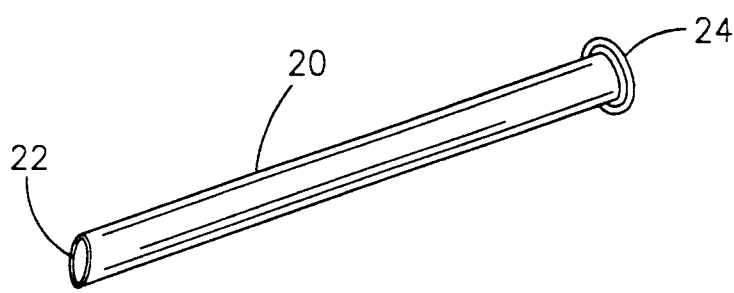
FIG. 3
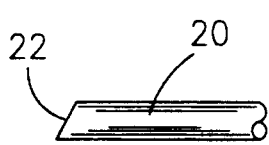 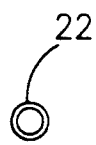 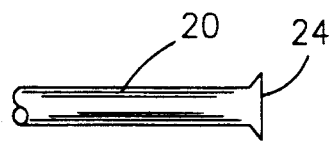 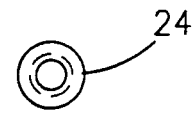
FIG. 4   FIG. 5   FIG. 6   FIG. 7
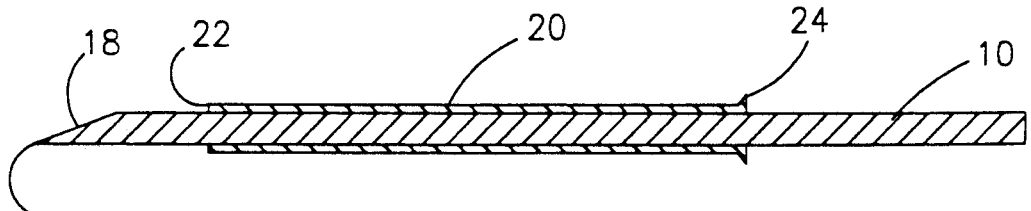
FIG. 8

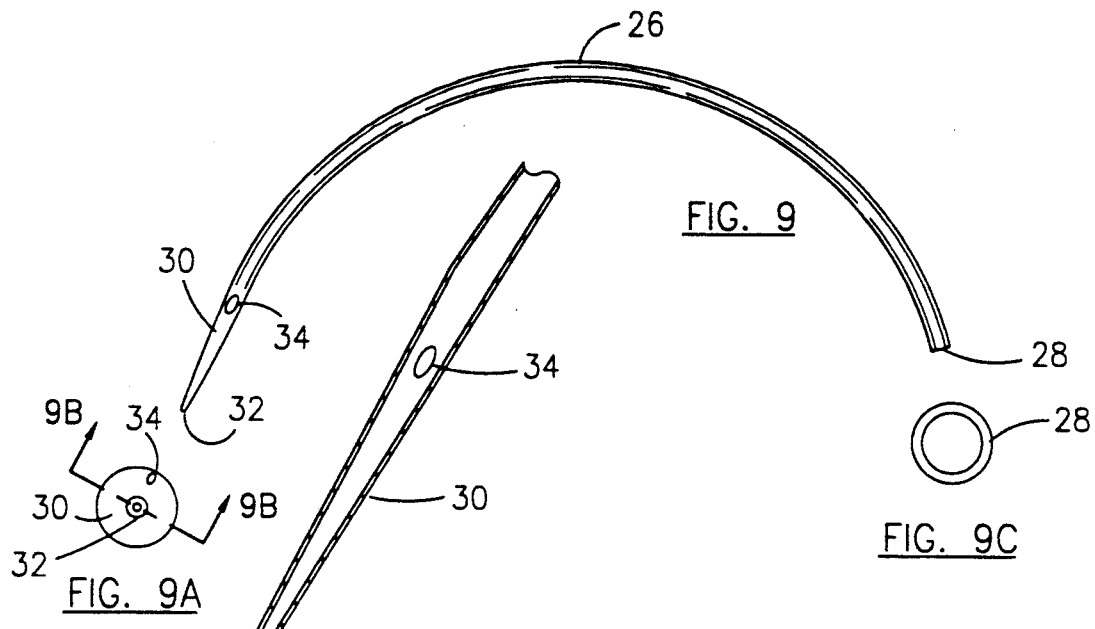
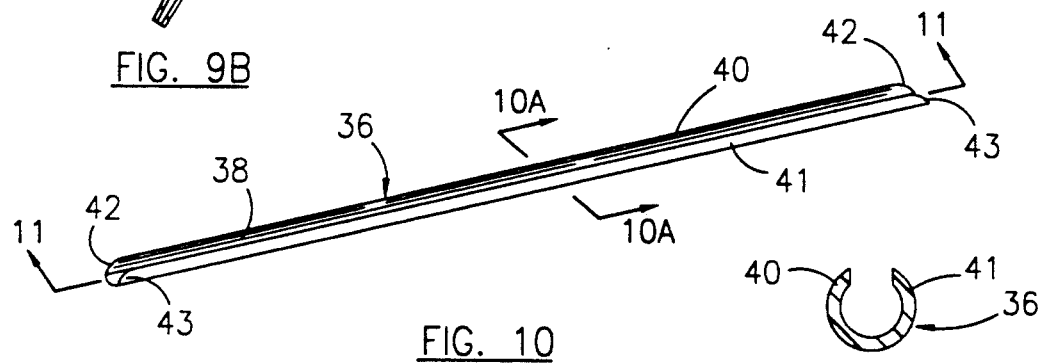
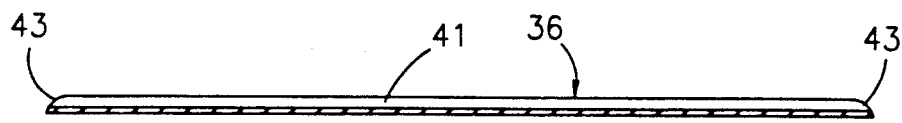

TRANSPYLORIC JEJUNOSTOMY CANNULATING SYSTEM

BACKGROUND OF THE INVENTION

The present invention is directed generally to a transpyloric jejunostomy cannulating apparatus and method to enable an operating surgeon to safely and rapidly cannulate the jejunum via a Stamm gastrostomy.

A reaction to major surgery is that stomach function may be impaired for up to ten days. On the other hand, the body needs to absorb nutrition immediately after surgery in order to promote healing. Furthermore, the nonfunctioning unfed gut can become a source of bacteria that gets into the blood stream. These problems are resolved by the introduction of nutrients through a jejunal tube properly inserted through the abdominal wall, gastric wall, pylorus and duodenum of a patient, into the jejunum beyond the ligament of Treitz.

Transpyloric passage of a jejunal tube is technically difficult to achieve because of at least the following anatomic problems. First, the pylorus and duodenum are in the retroperitoneum covered by small bowel mesentery and the right colon, making them poorly accessible to the surgeon's fingers. Secondly, the mucosa of the duodenum is redundant and creates ridges that prevent easy passage of a catheter.

Prior devices are known that are designed to span the pylorus, but all have certain shortcomings. The Moss dual lumen gastrostomy tube, as described in Moss, U.S. Pat. Nos. 4,543,089 and 4,642,092, is intended for transpyloric feeding. However, the tube does not go beyond the duodenum. Since the tip of the Moss tube is situated just beyond the pylorus, nutrients from the tube tend to go back to the stomach rather than moving on to the jejunum. Accordingly, the Moss tube has proved of little benefit to critically ill patients who have had major surgical illness.

The Nyhus-Nelson system is a tube with two balloons that allow the surgeon to do a "push-me/pull-me" technique of passing a tube through the duodenum. This system has the disadvantage of being very time consuming for the surgeon and having a relatively high rate of failure.

Cook Incorporated markets a Carey-Alzate-Coons double lumen gastrojejunostomy set, as described in U.S. Pat. No. 4,581,025 and Re 31,855, wherein the catheter is advanced over a wire guide after insertion of the wire guide through the pylorus and into the duodenum. The Cook device is designed for placement by a radiologist or gastroenterologist with access to an x-ray machine but is not suited for use at the operating table by a surgeon during major abdominal surgery. p Finally, Ross Laboratories produce a gastrostomy tube with an inner cannula that can be pushed through the pylorus by an endoscopist. This system has the disadvantage of requiring endoscopy and is prone to failure because when the endoscope is removed, the tube often comes back with it.

Feeding tubes of the type used in the present invention are marketed by Medical Innovations Corporation and disclosed in U.S. Pat. Nos. 4,685,901 and 4,701,163. The present invention facilitates placement of the feeding tube by a surgeon.

Accordingly, the inventors named herein have developed a transpyloric jejunostomy cannulating system which resolves the shortcomings of the devices described above. The system is based upon initial developments of Martin J. Winkler, M.D. as recorded in Disclosure Document No. 255713 received in the Patent and Trademark Office on Jun. 20, 1990 and in Disclosure Document No. 256401 received in the Patent and Trademark Office on Jun. 25, 1990.

A primary objective of the invention is to provide rapid, clean and atraumatic passage of a transpyloric jejuno-gastrostomy catheter from the skin through the abdominal wall, through the gastric wall, through the pylorus and duodenum, into the jejunum beyond the ligament of Treitz.

Another objective is to provide early nutritional support and calories for a traumatized patient immediately following surgery.

Another objective is to provide a transpyloric jejunostomy cannulating system which enables a feeding tube to be placed quickly for the sake of both the patient and doctor.

Another objective is to provide atraumatic insertion of a jejunal feeding tube with a minimum loss of blood.

A further objective of the invention is to provide a transpyloric jejunostomy cannulating system which provides for aspirating the stomach contents to prevent stomach fluid from contaminating the peritoneal cavity at the time the tube is placed by the surgeon Finally, an objective of the invention is to provide a transpyloric jejunostomy cannulating system based upon a combination of simple and rugged devices which are economical to manufacture and which are efficient in operation.

SUMMARY OF THE INVENTION

The transpyloric jejunostomy cannulating apparatus of the invention includes an abdominal wall trocar comprising an elongated shaft having a sharpened tapered end for atraumatic passage through the tissues of the abdominal wall. The trocar is preferably inserted from inside to out so as to avoid lacerating abdominal viscera and to provide a clean, atraumatic incision that will heal better. A tubular sheath receives the trocar for telescopic sliding movement therein. The sheath is a size and shape to closely conform to the trocar for passage through the abdominal wall with it.

An elongated generally tubular gastrostomy introducer has one end adapted for connection to a suction source and a free end portion tapering toward a free end of reduced width for insertion through the gastric wall into the lumen of the stomach. The introducer has an inlet opening adjacent its free end for aspiration of the stomach. An elongated slotted cannulator which is generally C-shaped in transverse cross section, has an external width for passage through the sheath after removal of the trocar, and an internal width to accommodate passage of the introducer therethrough. The cannulator is of a size and shape to closely conform to the introducer for passage through the gastric wall with it.

Finally, an elongated flexible feed tube is provided which is of a length and width for insertion within the cannulator through the abdominal wall, gastric wall, pylorus and duodenum into the jejunum beyond the ligament of Treitz.

The cannulator has sufficient column strength for passage of one end through the pylorus upon manipulation of the opposite end from a position externally of the gastric wall. The cannulator has a continuous longitudinal slot of a circumferential expanse of preferably between 70° and 80° to enable the feed tube to be radially peeled from the cannulator through the slot upon withdrawal of the cannulator after placement of the feed tube. The inlet opening of the introducer is preferably positioned on the tapering free end portion so that the introducer is positionable within the cannulator, such that the inlet opening is covered by but spaced from the cannulator for operation as a sump to prevent clogging of the inlet opening upon aspiration of the stomach. The cannulator should be at least 25 centimeters long and preferably about 32 centimeters. The feed tube includes a securement device for securing it relative to the gastric wall and the length of the feed tube from the securement device to the proximal free end should be at least 35 centimeters and preferably about 45 centimeters to assure proper placement of the free end for effective nutritional support.

The invention is furthermore directed to the method for atraumatic placement of an elongated flexible feed tube through the abdominal wall, gastric wall, pylorus and duodenum of a patient into the jejunum beyond the ligament of Treitz, including the steps of telescopically sliding the sheath onto the trocar, thrusting the trocar and sheath together through the abdominal wall, and removing the trocar from the sheath. Next, the gastric wall is punctured at a position for alignment with the puncture wound in the abdominal wall and the gastrostomy introducer is inserted through the gastric wall puncture into the lumen of the stomach and the stomach contents are aspirated. The slotted cannulator is then fit onto the introducer and passed through the gastric wall puncture into the stomach. Upon withdrawing the introducer from the stomach through the cannulator, the cannulator is manipulated externally of the stomach to move the inner end of the cannulator through the pylorus of the patient. Finally, the feed tube is inserted through the sheath in the abdominal wall, after which the sheath is removed, so that the feed tube may then be inserted into the cannulator and advanced through the stomach, pylorus and duodenum into the jejunum beyond the ligament of Treitz. The cannulator is then withdrawn through the gastric wall puncture while simultaneously peeling the feed tube from the cannulator through the longitudinal slot therein, so that the feed tube is maintained in its inserted position. Finally, the feed tube is secured relative to the abdominal wall.

BRIEF DESCRIPTION OF THE DRAWINGS

FIG. 1 is a perspective view of the abdominal wall trocar of the invention;

FIG. 2 is a side elevational view of the sharpened end of the trocar;

FIG. 3 is a perspective view of the tubular sheath for receiving the trocar of the invention;

FIG. 4 is a side elevational view of the beveled end of the sheath;

FIG. 5 is an end view of the beveled end of the sheath;

FIG. 6 is a partial side elevational view of the flanged end of the sheath;

FIG. 7 is an end view of the flanged end of the sheath;

FIG. 8 is a side sectional view of the sheath with the abdominal wall trocar telescopically received therein;

FIG. 9 is a perspective view of the gastrostomy introducer of the invention;

FIG. 9A is an end view of the tapering free end portion of the introducer;

FIG. 9B is a partial enlarged sectional view of the tapering free end portion of the introducer, as seen along line 9B in FIG. 9A;

FIG. 9C is an enlarged end view of the outer end of the introducer;

FIG. 10 is a perspective view of the elongated slotted cannulator of the invention;

FIG. 10A is a sectional view through the cannulator as taken along line 10A—10A in FIG. 10;

FIG. 11 is a side elevational view of the elongated slotted cannulator as taken along line 11—11 in FIG. 10;

DESCRIPTION OF A PREFERRED EMBODIMENT

Figure 12:
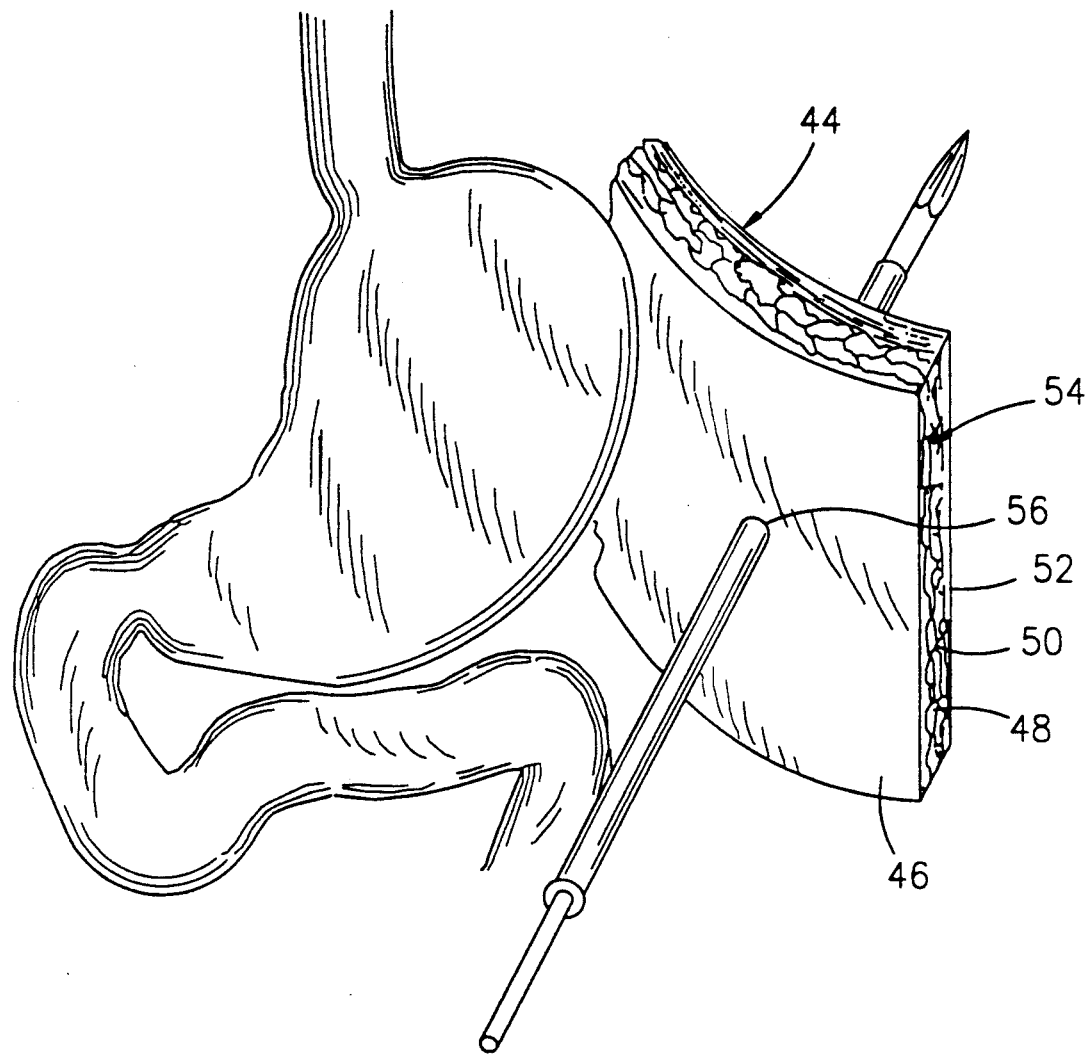
FIG. 12 is a diagrammatic view showing the trocar and sheath combination inserted, inside to out, through the abdominal wall.

The transpyloric jejunostomy cannulating apparatus of the invention includes several distinct devices including an abdominal wall trocar 10 shown in FIGS. 1 and 2. The trocar 10 is illustrated as an elongated length of a rigid rod, round in cross section and having a sharpened end 12. The sharpened end may be formed by a pair of angled machined cutting faces 14 and 15 which result in the formation of an extremely sharp tip 16 and cutting edge 18. The sharpened end 12 of the trocar may be alternately shaped so long as it provides an extremely sharp tip and cutting edge for atraumatic passage through the abdominal wall. It is believed that atraumatic passage utilizing a sharp trocar will lead to a decreased rate of gastro-cutaneous fistula. The trocar may be made of aluminum, stainless steel or any other suitable material.

FIG. 3 illustrates the tubular sheath 20 which is adapted to receive the trocar 10 for telescopic sliding movement therein as illustrated in FIG. 8. The sheath 20 is of a size and shape to closely conform to the trocar for passage through an abdominal wall with it. One end 22 of the sheath is beveled or cut at an angle to facilitate passage through the abdominal wall with the trocar.

FIG. 5 illustrates the round tubular cross section of the sheath and FIGS. 6 and 7 illustrate the opposite flanged end 24 of the sheath. The length of the sheath is not critical to the invention and a preferred length is approximately 20 centimeters. The sheath is preferably made of a semi rigid plastic material.

FIG. 9 illustrates the elongated tubular gastrostomy introducer 26 which has one end 28 adapted for connection to a suction source and an opposite free end portion 30 tapering toward a free end 32 of reduced width for insertion through the gastric wall of a patient into the lumen of the stomach. The free end is preferably open as illustrated in FIGS. 9A and 9B and an additional larger inlet opening 34 is provided on the tapering free end portion 30 for use as a sump for aspirating the stomach.

FIGS. 10, 10A and 11 taken along lines 10A—10A and 11—11 respectively of FIG. 10, illustrate the elongated slotted cannulator 36 of the invention. Cannulator 36 is generally C-shaped in transverse cross section as illustrated in FIG. 10A. It has an external Width for passage through the sheath 20 and an internal width to accommodate passage of the introducer 26 through it. The cannulator is of a size and shape to closely conform to the introducer 26 for passage through the gastric wall much like the sheath 20 conforms to the trocar 10 for passage together through the abdominal wall. The cannulator is preferably made of a semirigid plastic material such as polyethylene, but could be made of various suitable materials. It is designed to be disposable and somewhat flexible. It is important that the cannulator 36 have sufficient column strength for passage of one end through the pylorus of a patient, as described hereinbelow, upon manipulation of the opposite end from a position externally of the gastric wall. Note that the cannulator has a continuous longitudinal slot 38 of a circumferential expanse sufficient to enable the feed tube, described below, to be peeled from the cannulator through the slot. The circumferential expanse of the slot 38 is generally between 45° and 90° and preferably between 70° and 80°. To facilitate passage of the cannulator through the gastric wall with the introducer 26, the opposite side walls 40 and 41 of the cannulator 36 have rounded tapered ends as indicated at 42 and 43. The length of the cannulator 36 is preferably at least 25 centimeters and a preferred length is approximately 32 centimeters.

The method of using the transpyloric jejunostomy cannulating system of the invention is illustrated in FIGS. 12 through 20. FIG. 12 shows the sheath 20 telescopically fit onto the trocar 10 with both being inserted through the abdominal wall by an inside-to-out stab wound. The extremely sharp tip and cutting edge of the trocar 10 enable atraumatic passage through the tissues of the abdominal wall including the peritoneum 46, abdominal wall muscles and facia 48, subcutaneous fat 50 and skin 52. The trocar is preferably inserted through the abdominal wall at an oblique angle so that the passage through the abdominal wall is longer than the thickness of the abdominal wall. The formation of a long submuscular and subcutaneous tunnel by the trocar allows optimum sitting of the peritoneal puncture wound 54 as well as the exit site wound through the skin. Optimum sitting of the peritoneal puncture should allow for good approximation of the fundus of the stomach to the peritoneum 46. Optimal sitting of the skin exit sites should allow the exit to be well away from the incision 56 and well away from other stomas or drains that the surgeon might employ. It is believed that the long oblique tunnel is further advantageous for decreasing the incidence of gastro-cutaneous fistula After puncturing the abdominal wall 44 the trocar 10 is withdrawn and a feed tube 58, described in further detail below, is inserted through the sheath. Sheath 20 may then be withdrawn. Since the flanged end 24 of the sheath is on the interior end, it does not interfere with withdrawal of the sheath through the abdominal wall.

Next, a puncture site on the gastric wall 60 of stomach 62 should be located at a position for registration with the peritoneal puncture formed by the trocar 10. The gastric wall hole 64 is preferably made by electrocautery to thereby form a very small hole through which the free end 32 of the introducer 26, having a diameter of only about 2 millimeters, can be inserted. As the introducer is pushed through the hole 64, the expanding width of the tapered free end dilates the hole to form somewhat of a seal around the introducer to prevent leakage of stomach fluids. Furthermore, a purse string suture 66 around the gastric wall hole 64 further contributes to the sealed relation between the introducer 26 and gastric wall hole 64. Whereas the tapered free end 30 of introducer 26 is flexible, it is stiff enough to push through the hole 64 while, at the same time, being soft enough that, when pushed through the gastric wall, it won't pierce the opposite side of the stomach. Upon initial insertion of the introducer 26 through the gastric wall hole 64, the outer end of introducer 26 is connected to a suction source and a surgeon's index finger covers the inlet opening 34. The open free end 32 of introducer 26 thus enables the flashback of bile or gastric juice into the introducer to provide the surgeon with a visible indicator that the introducer is properly positioned in the lumina of the stomach. To facilitate emptying of a stomach, the cannulator 36 is snapped onto the introducer 26 and slid down the introducer toward the free end to the extent indicated in FIG. 16 wherein the inlet opening 34 is covered by, but spaced from the cannulator, as also shown in section in FIG. 15. Thus an efficient "sump" is created. This "sump" suction allows rapid gastric emptying of vegetable matter, air, gastric secretions, inspissated mucous without fowling of the suction system. Additionally, the introducer 26 may be reciprocated back and forth within the stomach to prevent clogging of the inlet opening 34. Thus the introducer 26 provides for rapid cannulation of the stomach in order to create a Stamm gastrostomy. It also provides for atraumatic entry into the stomach without false passage within the layers of the gastric wall and without hemorrhage from the rich blood supply of the gastric wall. Finally, the introducer 26 provides for "clean" cannulation and decompression of the stomach without spillage of gastric contents.

Figure 13:
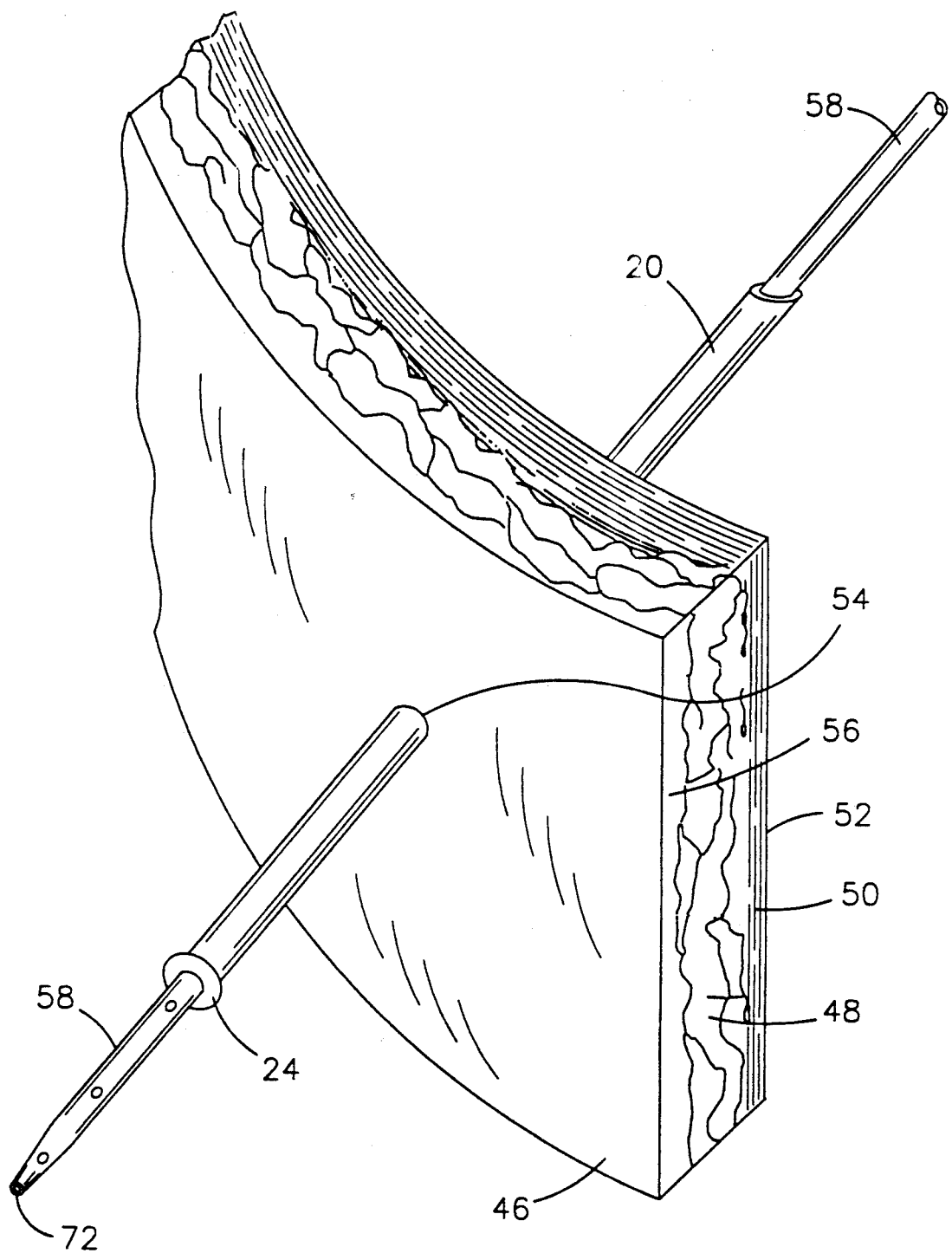
FIG. 13 is an enlarged diagrammatic view showing the feed tube inserted through the sheath in the abdominal wall after removal of the trocar.
Figure 14:
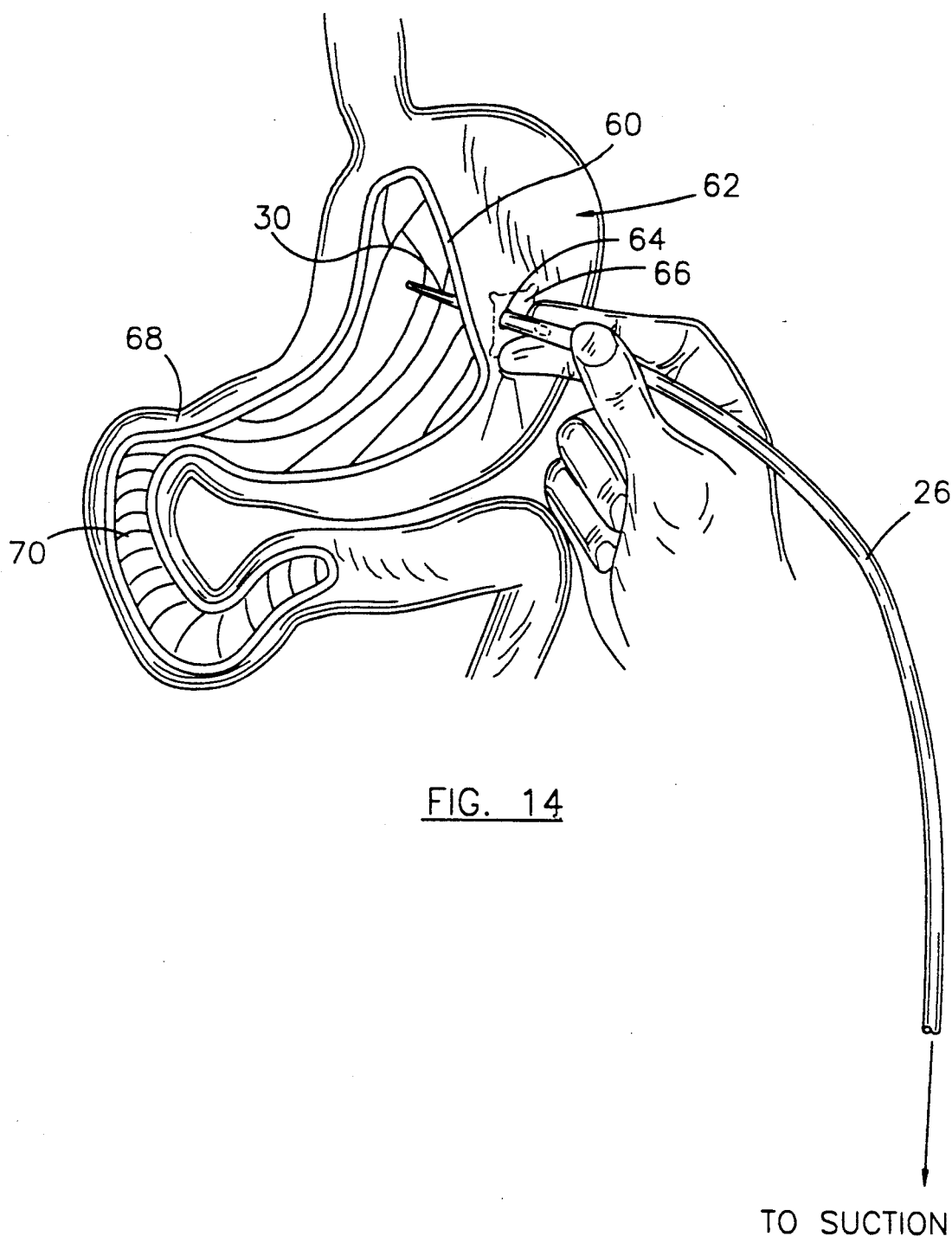
FIG. 14 is a diagrammatic view showing the tubular gastrostomy introducer being inserted through the gastric wall into the lumen of the stomach.
Figure 15:
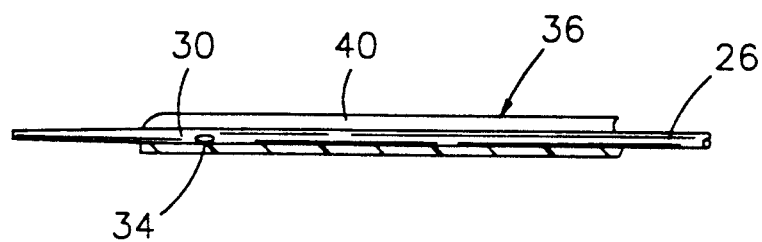
FIG. 15 is a partial sectional end view showing the cannulator positioned over an inlet opening of the introducer, but spaced therefrom for operation as a sump.
Figure 16:
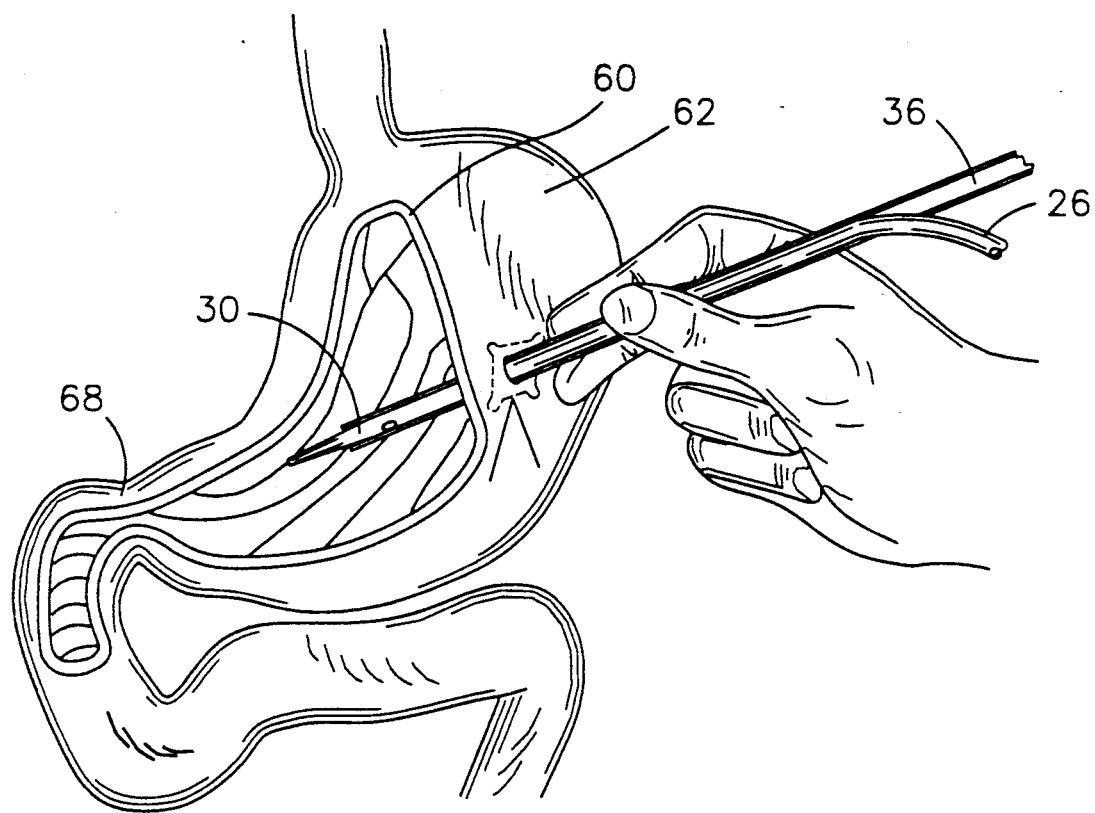
FIG. 16 shows the introducer and cannulator operating in combination as a sump to aspirate the stomach.
Figure 17:
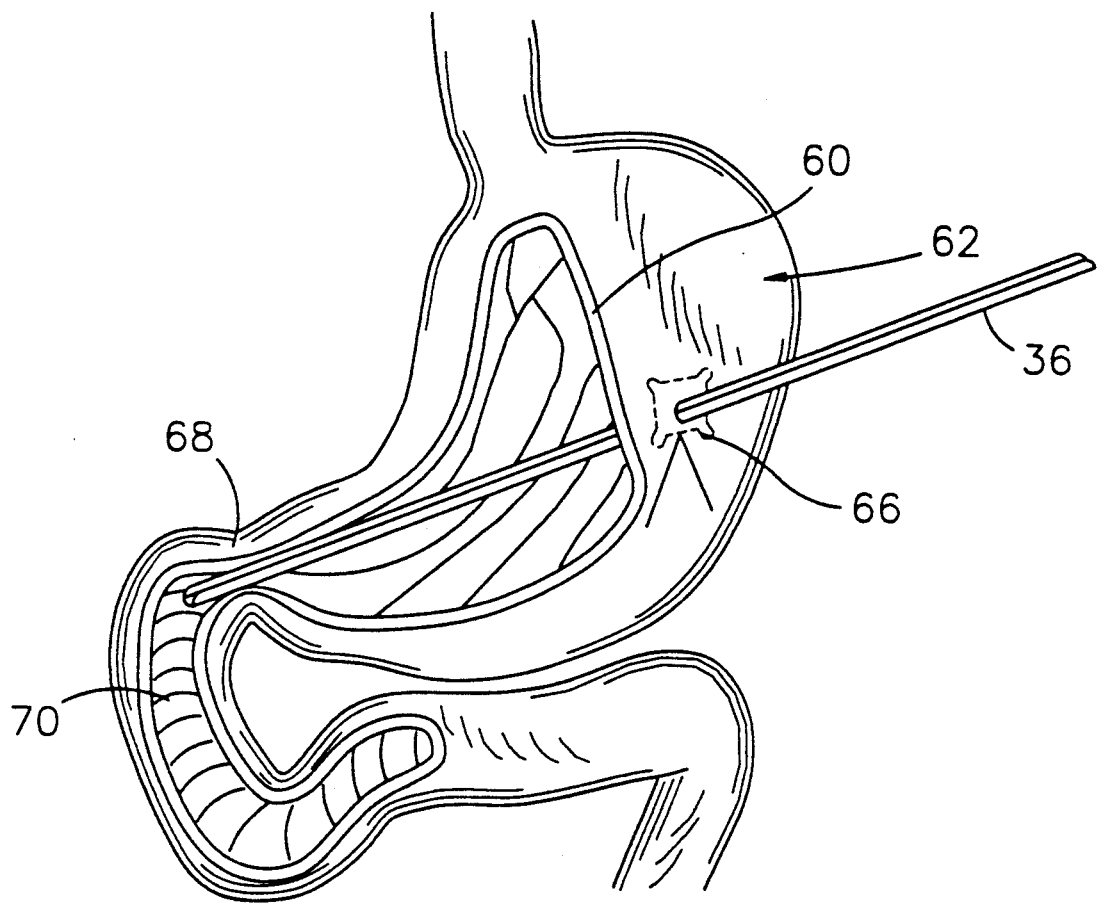
FIG. 17 is a diagrammatic illustration showing the cannulator protruding through the pylorus after removal of the introducer.
Figure 18:
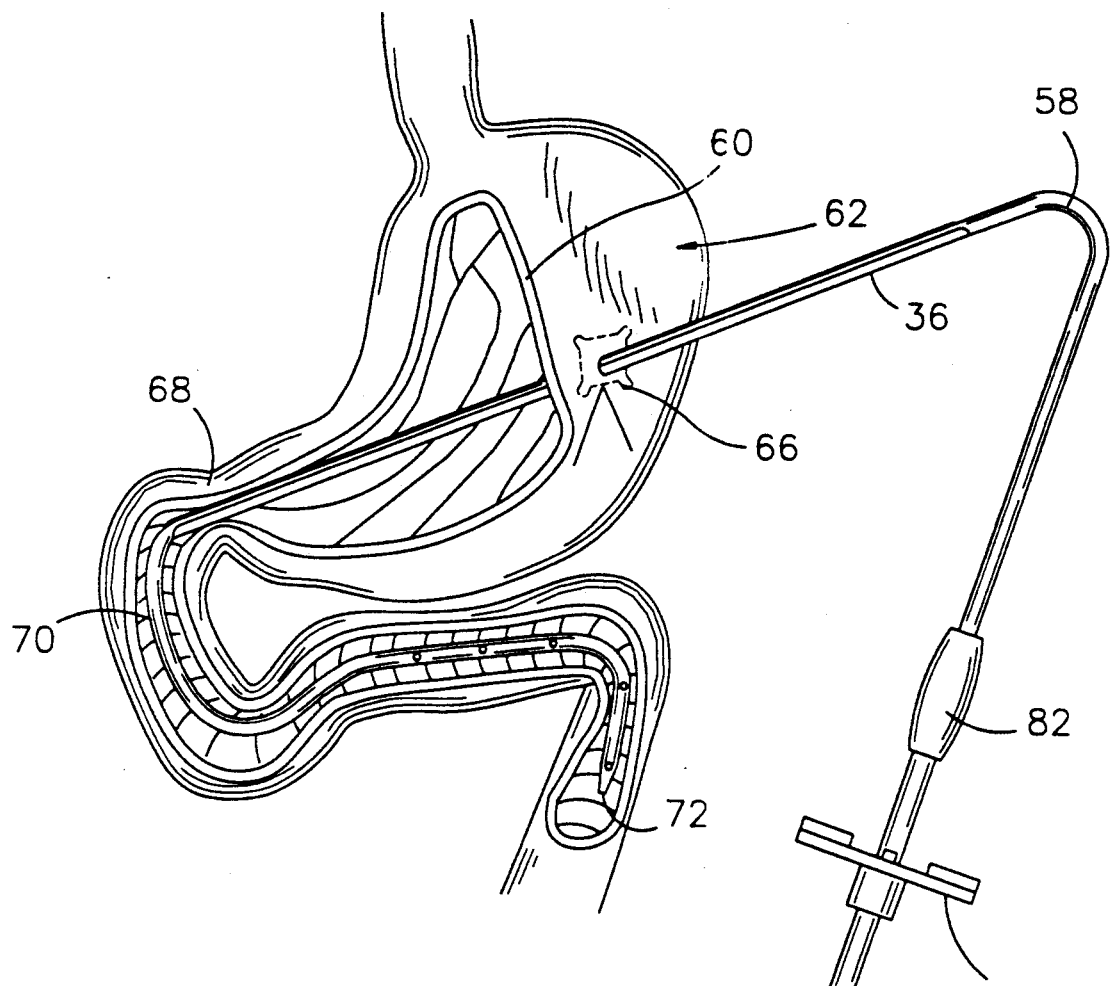
FIG. 18 is a diagrammatic illustration showing the insertion of the feed tube through the cannulator beyond the pylorus and into the duodenum.
Figure 19:
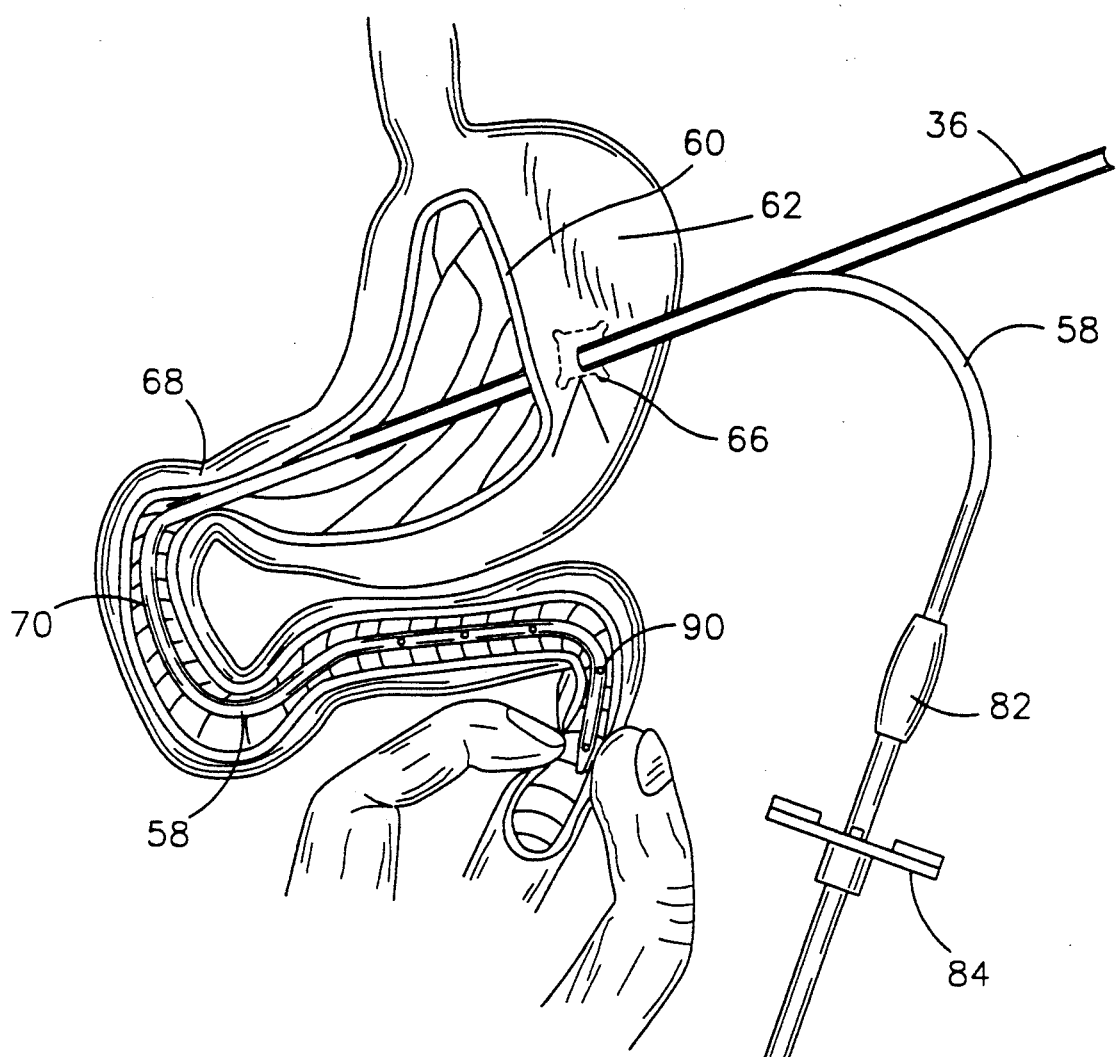
FIG. 19 is a diagrammatic illustration of the cannulator being withdrawn from the gastric wall with the feed tube being peeled from the longitudinal slot of the cannulator.

When the stomach is emptied, the introducer 26 is withdrawn from the stomach through the cannulator 36. The cannulator 36 is then manipulated by the surgeon externally of the stomach to move the inner end of the cannulator through the pylorus. The feed tube 58, which was previously inserted through the abdominal wall as shown in FIG. 13, is then passed within the cannulator through the gastric wall 60 and pylorus 68 into the duodenum 70. The proximal or free end 72 of the feed tube 58 is soft and round so as not to pierce the retro-peritoneal duodenum as the feed tube is further advanced through the cannulator 36. On the other hand, the feed tube has sufficient column strength to follow around the curves of the duodenum. This is important because portions of the duodenum are inaccessible by the surgeon's fingers since they are covered by other organs. Feed tube 58 is continually advanced through the duodenum into the jejunum beyond the ligament of Treitz 100 as shown in FIG. 19. At this position, the surgeon's fingers can pinch the jejunum to feel the position of the free end of the feed tube 58 therein.

Upon proper placement of the feed tube, the cannulator 36 is then withdrawn from the gastric wall hole 64 while the portion of the feed externally of the gastric wall is peeled from the cannulator 36 through slot 38. Thus the cannulator 36 enables rapid "blind" cannulation of the retro-peritoneal duodenum with passage of the jejunal tube beyond the ligament of Treitz into the proximal jejunum. This "blind" passage of the jejunal tube is dependable in that, in an initial clinical study, the surgeon was able to cannulate the jejunum in 90% of the patients. The primary purpose of the transpyloric cannulator is to provide atraumatic passage of the transpyloric feed tube 58 with a particular emphasis on the prevention of laceration or perforation of the retro-peritoneal duodenum during this procedure.

Figure 20:
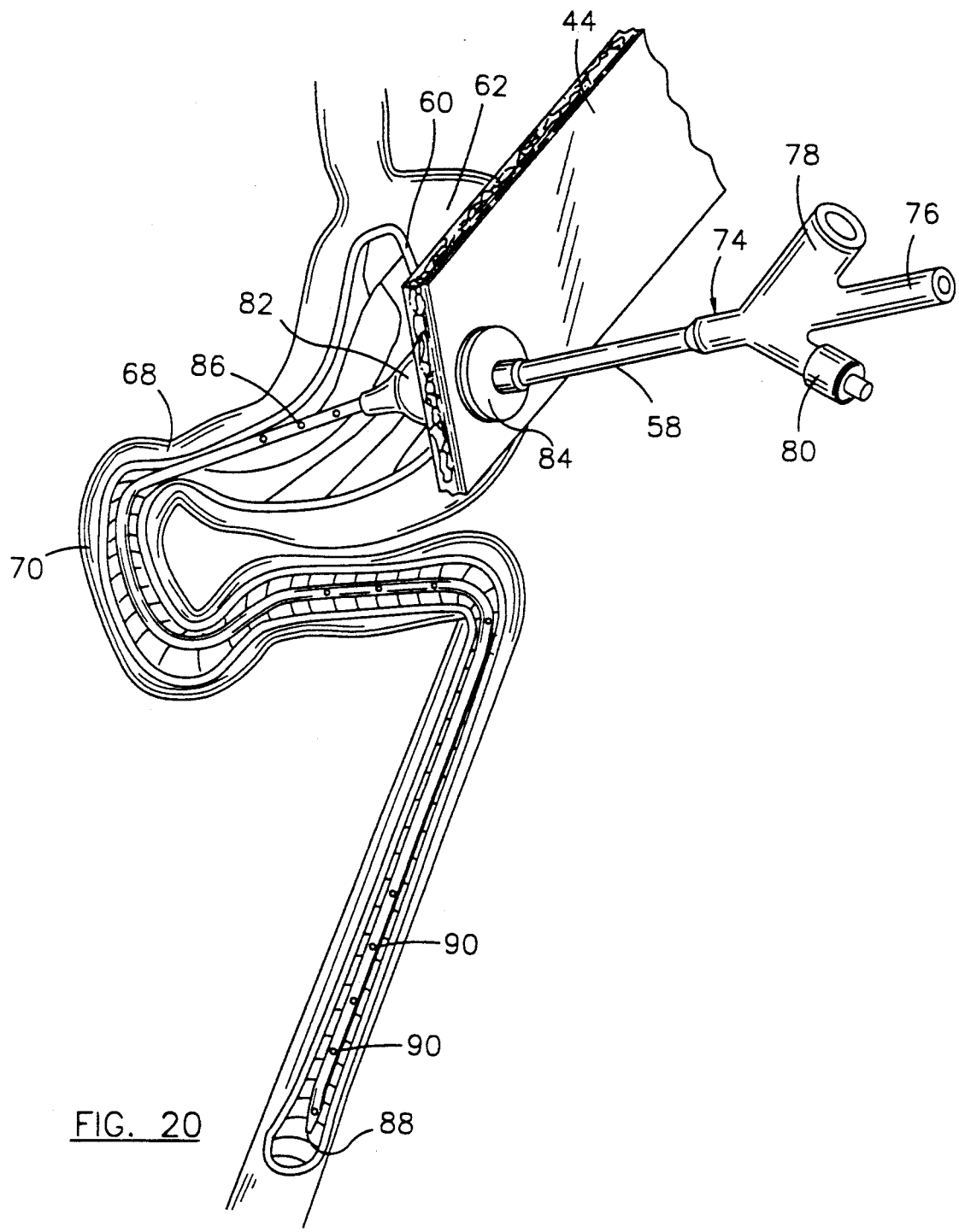
FIG. 20 is a diagrammatic illustration of the feed tube secured relative to the abdominal wall with the free end of the feed tube positioned in the jejunum beyond the ligament of Treitz for effective nutritional support.

Feed tube 58 terminates at its outer end in a fitting 74 having a central vacuum source connector 76, a feeding attachment 78 and an inflation attachment 80. These are used for the securement and operation of the feed tube after insertion of the feed tube as described above. An inflatable balloon sleeve 82 on feed tube 58 is advanced through the gastric wall hole 64 into the stomach. A source of pressurized saline is attached to inflation attachment so for inflating the balloon as illustrated in FIG. 20. A flexible securement ring 84 on the feed tube upstream of the balloon is then frictionally slid along the tube and secured against the abdominal wall with both the gastric wall 60 and abdominal wall 44 sandwiched between the balloon sleeve 82 and ring 84 as shown in FIG. 20. The frictional grip of the securement ring 84 on the feed tube serves to maintain the feed tube in its intended position. The vacuum source connector 76 communicates with a series of suction holes 86 through the side wall of the feed tube just down stream of balloon sleeve 82 for aspirating the stomach when needed. The feeding attachment 78 communicates through an internal lumen with the inner end of the feed tube 58 for dispensing nutrients through both the open end of the feed tube and a series of axially spaced apart feeding holes 90 through the side wall thereon. The length of the feed tube 58 from the free inner end to the balloon sleeve 82 is preferably approximately 45 centimeters. This length will enable the fully inserted free end to extend into the jejunum beyond the ligament of Treitz 100 where nutritional support is most effectively administered.

Feeding tubes of the type described are disclosed in Parks, U.S. Pat. Nos. 4,685,901 and 4,701,163. An important feature of the feed tube 58 for purposes of the present invention is that the length from the securement device, such as balloon sleeve 82, to the free end 72 be sufficient for placement of the free end in the jejunum beyond the ligament of Treitz 100. The distal portion of the jejunal feed tube 58 preferably has radio-opaque material within its wall to allow postoperative visualization on subsequent X-rays.

Whereas the invention has been shown and described in connection with a preferred embodiment thereof, it is understood that many modifications, additions, and substitutions may be made which are within the intended broad scope of the appended claims. For example, it is apparent that the system of the present invention could be used for the insertion of tubes other than feeding tubes.

Thus there has been shown and described a transpyloric jejunostomy cannulating system which accomplishes at least all of the stated objects.

We claim:

1. A transpyloric jejunostomy cannulating apparatus for insertion through the abdominal wall, gastric wall, pylorus and duodenum of a patient, into the jejunum beyond the ligament of Treitz, said apparatus comprising, an abdominal wall trocar comprising an elongated shaft having a sharpened tapered end, a tubular sheath adapted to receive said trocar for telescopic sliding movement therein, said sheath being of a size and shape to closely conform to said trocar for passage through an abdominal wall therewith, an elongated generally tubular gastrostomy introducer having one end adapted for connection to a suction source and a free end portion tapering toward a free end of reduced width for insertion through the gastric wall into the lumen of a stomach, said introducer having an inlet opening adjacent said free end, an elongated slotted cannulator, generally C-shaped in transverse cross section, and having an external width for passage through said sheath and an internal width to accommodate passage of said introducer therethrough, said cannulator being of a size and shape to closely conform to said introducer for passage through a gastric wall therewith, and an elongated flexible feed tube of a length and width for insertion within said cannulator through the abdominal wall, gastric wall pylorus, and duodenum into the jejunum beyond the ligament of Treitz.

2. The apparatus of claim 1 wherein said cannulator has sufficient column strength for passage of one end through the pylorus upon manipulation of the opposite end from a position externally of the gastric wall.

3. The apparatus of claim 2 wherein said cannulator has a continuous longitudinal slot of a circumferential expanse sufficient to enable said feed tube to be radially peeled from the cannulator through said slot.

4. The apparatus of claim 2 wherein said cannulator has a continuous longitudinal slot of a circumferential expanse of between 45° and 90°.

5. The apparatus of claim 4 wherein the circumferential expanse of said longitudinal slot is between 70° and 80°.

6. The apparatus of claim 4 wherein said cannulator is formed of a semi-rigid resilient plastic material.

7. The apparatus of claim 4 wherein said cannulator has a pair of opposite side walls, each having tapered opposite ends.

8. The apparatus of claim 7 wherein said cannulator has a length of at least 25 centimeters.

9. The apparatus of claim 1 wherein the inlet opening of said introducer is positioned on said tapering free end portion such that said introducer is positionable within said cannulator such that said inlet opening is covered by but spaced from said cannulator for operation as a sump to prevent clogging of said inlet opening upon aspiration of the stomach.

10. The apparatus of claim 9 wherein said introducer further comprises a second smaller inlet opening adjacent said free end of the introducer.

11. The apparatus of claim i wherein one end of said tubular sheath is beveled to facilitate passage through an abdominal wall.

12. The apparatus of claim 11 wherein the opposite end of said tubular sheath includes a radially outwardly protruding lip.

13. The apparatus of claim 1 wherein said feed tube has a soft generally rounded proximal free end to facilitate passage through the duodenum.

14. The apparatus of claim 1 wherein said feed tube includes securement means therealong operative to secure said tube relative to a gastric wall, the length of said feed tube from said securement means to said proximal end being at least 35 centimeters 15. The apparatus of claim 14 wherein the length of said feed tube from said securement means to said proximal end is approximately 45 centimeters.

16. A transpyloric jejunostomy cannulating apparatus for atraumatic placement of an elongated flexible feed tube through the abdominal wall, gastric wall pylorus an duodenum of a patient into the jejunum beyond the ligament of Treitz, said apparatus comprising,
    an abdominal wall trocar comprising an elongated shaft having a sharpened tapered end,
    a tubular sheath adapted to receive said trocar for telescopic sliding movement therein, said sheath being of a size and shape to closely conform to said trocar for passage through an abdominal wall therewith,
    an elongated generally tubular gastrostomy introducer having one end adapted for connection to a suction source and a free end portion tapering toward a free end of reduced width for insertion through the gastric wall into the lumen of a stomach, said introducer having an inlet opening adjacent said free end,
    an elongated slotted cannulator, generally C-shaped in transverse cross section, and having an external width for passage through said sheath and an internal width to accommodate passage of said introducer therethrough and having a length sufficient to extend through said pylorus while maintaining sufficient length external to said gastric wall for manipulation of said cannulator,
    said cannulator being of a size and shape to closely conform to said introducer for passage through a gastric wall therewith, and
    said cannulator, upon withdrawal of the introducer therefrom, affording a sufficiently rigid guide for passage of a flexible feed tube through the pylorus of a patient.

17. The apparatus of claim 16 wherein said cannulator has sufficient column strength for passage of one end through the pylorus upon manipulation of the opposite end from a position externally of the gastric wall.

18. The apparatus of claim 17 wherein said cannulator has a continuous longitudinal slot of a circumferential expanse sufficient to enable said feed tube to be radially peeled from the cannulator through said slot.

19. The apparatus of claim 16 wherein said cannulator has a length of at least 25 centimeters inches.

20. The apparatus of claim 16 wherein said elongated slotted cannulator comprises a single integral member having a circumference of at least 180°.

21. A method for atraumatic placement of an elongated flexible feed tube through the abdominal wall, gastric wall, pylorus and duodenum of a patient into the jejunum beyond the ligament of Treitz, said method comprising,
    providing an abdominal wall trocar, an elongated tubular sheath of a size and shape to closely conform to said trocar, an elongated tubular gastrostomy introducer having a tapered free end with an inlet opening therethrough, an elongated slotted cannulator insertable through said sheath and having a longitudinal slot and internal width to accommodate passage of the introducer therethrough, and an elongated flexible feed tube,
    telescopically sliding said sheath onto said trocar,
    thrusting said trocar and sheath together through the abdominal wall to form a puncture wound therethrough,
    removing said trocar from said sheath,
    puncturing the gastric wall at a position for alignment with the puncture wound in the abdominal wall,
    inserting said gastrostomy introducer through the gastric wall puncture into the lumen of the stomach,
    aspirating the stomach through said introducer,
    fitting the slotted cannulator onto said introducer and pass said cannulator through the gastric wall puncture into the stomach,
    withdrawing said introducer from the stomach through said cannulator,
    manipulating said cannulator externally of the stomach to move the end of the cannulator within the stomach through the pylorus of the patient,
    inserting said feed tube through the sheath in the abdominal wall,
    inserting said feed tube into said cannulator and advancing the end of the feed tube through the stomach, pylorus and duodenum into the jejunum beyond the ligament of Treitz,
    withdrawing said cannulator through said puncture and peeling said feed tube from said cannulator through the longitudinal slot therein whereby said feed tube is maintained in its inserted position, and
    securing said feed tube relative to said abdominal wall.

22. The method of claim 21 wherein thrusting said trocar and sheath through the abdominal wall is done in an inside to out direction thereby to protect the abdominal viscera from laceration.

23. The method of claim 22 wherein thrusting said trocar and sheath through the abdominal wall is done at an oblique angle to create a tunnel therethrough which is longer than the thickness of the abdominal wall.

24. The method of claim 21 further comprising making a purse string suture around the gastric wall puncture.

25. The method of claim 21 further comprising arranging said introducer within said cannulator so that the inlet opening of the introducer is covered by but spaced from the cannulator wall and connecting the external end of the introducer to a suction source for operation as a sump.

26. The method of claim 25 further comprising reciprocating said introducer and cannulator back and forth within the stomach, thereby to prevent clogging of the inlet opening.

27. A transpyloric jejunostomy cannulating apparatus for atraumatic placement of an elongated flexible feed tube through the abdominal wall, gastric wall, pylorus and duodenum of a patient into the jejunum beyond the ligament of Treitz, said apparatus comprising, an abdominal wall trocar comprising an elongated shaft having a sharpened tapered end, a tubular sheath adapted to receive said trocar for telescopic sliding movement therein, said sheath being of a size and shape to closely conform to said trocar for passage through an abdominal wall therewith, an elongated generally tubular gastrostomy introducer having one end adapted for connection to a suction source and a free end portion tapering toward a free end of reduced width for insertion through the gastric wall into the lumen of a stomach, said introducer having an inlet opening adjacent said free end, an elongated slotted cannulator, generally C-shaped in transverse cross section, and having an external width for passage through said sheath and an internal width to accommodate passage of said introducer therethrough, said cannulator being of a size and shape to closely conform to said introducer for passage through a gastric wall therewith, and said cannulator, upon withdrawal of the introducer therefrom, affording a sufficiently rigid guide for passage of a flexible feed tube through the pylorus of a patient, said cannulator having sufficient column strength for passage of one end through the pylorus upon manipulation of the opposite end from a position externally of the gastric wall, said cannulator having a continuous longitudinal slot of a circumferential expanse of between 45° and 90°.

28. The apparatus of claim 27 wherein the circumferential expanse of said longitudinal slot is between 70° and 80°.

29. The apparatus of claim 27 wherein said cannulator is formed of a semi-rigid resilient plastic material.

30. A transpyloric jejunostomy cannulating apparatus for atraumatic placement of an elongated flexible feed tube through the abdominal wall, gastric wall pylorus and duodenum of a patient into the jejunum beyond the ligament of Treitz, said apparatus comprising, an abdominal wall trocar comprising an elongated shaft having a sharpened tapered end, a tubular sheath adapted to receive said trocar for telescopic sliding movement therein, said sheath being of a size and shape to closely conform to said trocar for passage through an abdominal wall therewith, an elongated generally tubular gastrostomy introducer having one end adapted for connection to a suction source and a free end portion tapering toward a free end of reduced width for insertion through the gastric wall into the lumen of a stomach, said introducer having an inlet opening adjacent said free end, and wherein said inlet opening is positioned on said tapering free end portion such that said introducer is positionable within said cannulator such that said inlet opening is covered by but spaced from said cannulator for operation as a sump to prevent clogging of said inlet opening upon aspiration of said stomach;

an elongated slotted cannulator, generally C-shaped in transverse cross section, and having an external width for passage through said sheath and an internal width to accommodate passage of said introducer therethrough, said cannulator being of a size and shape to closely conform to said introducer for passage through a gastric wall therewith, and said cannulator, upon withdrawal of the introducer therefrom, affording a sufficiently rigid guide for passage of a flexible feed tube through the pylorus of a patient.

31. The apparatus of claim 30 wherein said introducer further comprises a second smaller inlet opening adjacent said free end of the introducer.

* * * * *